United States Patent [19]
Tan et al.

[11] Patent Number: 5,312,395
[45] Date of Patent: May 17, 1994

[54] METHOD OF TREATING PIGMENTED LESIONS USING PULSED IRRADIATION

[75] Inventors: Oon T. Tan, Boston; James C. Hsia, Andover; Horace Furumoto, Wellesley, all of Mass.

[73] Assignees: Boston University; Candela Laser Corp., both of Mass.

[21] Appl. No.: 933,873

[22] Filed: Aug. 21, 1992

Related U.S. Application Data

[63] Continuation of Ser. No. 493,309, Mar. 14, 1990, abandoned.

[51] Int. Cl.$^5$ .............................................. A61N 5/06
[52] U.S. Cl. .......................................... 606/9; 606/2; 606/3; 607/89; 607/94
[58] Field of Search ...................................... 606/9–19; 607/88–90, 94

[56] References Cited

U.S. PATENT DOCUMENTS 4,829,262  5/1989  Furumoto .............................. 606/2

OTHER PUBLICATIONS

"Selective Photothermolysis: Precise Microsurgery by Selctive Absorption of Patent Radiation" by Anderson et al; Science vol. 220 Apr. 1983 pp. 524–527.

K. A. Sherwood et al., "Selective Melanocyte Damage Using Pulsed Irradiation Over a Variety of Wavelengths", *Lasers in Surgery and Medicine*, vol. 8, No. 2, 1988, Abstract No. 209, p. 190 (American Society for Laser Medicine and Surgery's Eighth Annual Meeting held Apr. 25–27, 1988).

P. R. Morrison et al., "Intracellular Spectrophotometric Changes of Thermally Altered Red Blood Cells", *Lasers in Surgery and Medicine*, Supplement 2, 1990 Abstracts, Abstract No. 13, p. 6 (American Society for Laser Medicine and Surgery's Tenth Annual Meeting held Apr. 6–8, 1990).

O. T. Tan et al., "Laser Treatment of Portwine Stains", *Lasers in Surgery and Medicine*, Supplement 2, 1990 Abstracts, Abstract No. 229, p. 54 (American Society for Laser Medicine and Surgery's Tenth Annual Meeting held Apr. 6–8, 1990).

Reid, V. et al., "Q-switched Ruby laser treatment of black tatoos", *British Journal of Plastic Surgery*, pp. 455–459, (1983).

Polla, Luigi L. et al., "Melanosomes Are A Primary Target of Q-Switched Ruby Laser Irradiation in Guinea Pig Skin", *The Society For Investigative Dermatology*, pp. 281–286 (1987).

Dover, Jeffrey S. et al., "Pigmented Guinea Pig Skin Irradiated With Q-Switch Ruby Laser Pulses" *Arch Dermatol*, 125:42–49, (Jan. 1989).

Arndt, Kenneth A., "Treatment of Small Vascular and Pigmented Lesions with the Argon Laser", *Cutaneous Laser Therapy:Principles and Methods*, pp. 165–178 (1983).

Tan, Oon Tian et al., "Spotsize Effects on Guinea Pig Skin Following Pulsed Irradiation", *The Society For Investigative Dermatology*, pp. 877–881, (1988).

Murphy, George F. et al., "Organelle-Specific Injury to Melanin-Containing Cells in Human Skin by Pulsed Laser Irradiation", *Laboratory Investigation*, 49:6:680–685 (1983).

Goldman, Leon, et al., "The Laser in Dermatology", *Lasers in Medicine*, pp. 329–353, (1971).

Sherwood, K. A., "Effect of Wavelength on Cutaneous Pigment Using Pulsed Irradiation", The Society for Investigative Dermatology, pp. 717–720, (1989).

Margolis, Randall, J., "Visible Action Spectrum for Melanin-Specific Selective Photothermolysis", *Lasers in Surgery and Medicine*, 9;389–397 (1989).

Apfelberg, David B., et al., "Progress Report On Extended Clinical use of the Argon Laser for Cutaneous (List continued on next page.)

Primary Examiner—David M. Shay
Attorney, Agent, or Firm—Testa, Hurwitz & Thibeault

[57] ABSTRACT

A cutaneous pigmented lesion is treated by irradiation with laser light of between 345 and 600 nm and preferably about 500 nm wavelength. The fluence is between 1 and 10 J/Cm$^2$ and preferably between 2 and 4 J/cm$^2$. The pulse duration is less than 1 μsec and preferably less than 500 nsec. A 3 mm diameter spot is illuminated.

11 Claims, 1 Drawing Sheet

OTHER PUBLICATIONS

Lesions", *Lasers in Surgery and Medicine* 1:71–83 (1980).

Anderson, R. Rox et al., "Microvascular Can Be Selectively Damaged Using Dye Lasers: A Basic Theory and Experimental Evicence in Human Skin,", Lasers in Surgery and Medicine, 1:263–276 (1981).

Itzkan, Irving, Laser System for Providing Target Specific Energy Deposition and Damage, European Patent Application 0 172 490 (Aug. 7, 1984).

Sherwood, K. A., "Selective Melanocyte Damage Using Pulsed Irradiation Over Variety of Wavelengths", *Lasers in Surgery and Medicine* Supplement 2, 1990 Abstracts, #209, Apr. 6–8 (1990).

Kurban, A. K., "Pulse Effects On Cutaneous Pigment Ablation", *Lasers in Surgery and Medicine* Supplement 2, 1990 Abstracts, #213, Apr. 6–8 (1990).

Tan, O. T., "Treatment Of Superficial Benign Cutaneous Pigmented Lesions Using Pulsed Irradiation", *Lasers in Surgery and Medicine* Supplement 2, 1990 Abstracts, #215, Apr. 6–9 (1990).

Patent Cooperation Treaty, CAN89-13, Search Report.

METHOD OF TREATING PIGMENTED LESIONS USING PULSED IRRADIATION

This is a continuation of copending application ser. no. 07/493,309 filed on Mar. 14, 1990, now abandoned.

BACKGROUND OF THE INVENTION

Superficial benign cutaneous pigmented lesions such as lentigines, cafe' au lait and nevus spilus are commonly seen in dermatologic practice. A myriad of therapeutic modalities including liquid nitrogen, electrocautery and depigmenting chemicals have been used to remove them. Although widely used, none have succeeded in destroying the abnormal pigmented cells alone without damaging adjacent structures and producing adverse effects like hypopigmentation.

Over the last two decades, there have been several reports describing the removal of these pigmented lesions by a variety of lasers such as the excimer (351 nm), argon (488,514 nm), ruby (694 nm), Nd:YAG (1060 nm), and $CO_2$ (10,600 nm) lasers. However, there has generally been damage to both pigmented and nonpigmented cells. Pigmented lesions treated by laser have included lentigines, nevi, melanomas, oral hypermelanosis of Peutz-Jeghers syndrome, the nevus of Ota, and a lentigo maligns. The pigment depth of these laser-treated lesions has also varied significantly, from superficial lentigines in the epidermis to lesions lying deep in the reticular dermis like the nevus of Ota.

Previous studies reporting "successful" removal of pigmented lesions have relied on clinical assessment rather than on histology and have used widely divergent wavelengths, pulse durations, energy densities and spotsizes. There has been no effort to define laser parameters necessary for optimal removal of pigmented lesions.

Melanin, an endogenous cutaneous pigment which is most concentrated in the basal layer of the epidermis, has an absorption spectrum that is highest in the ultraviolet range and gradually diminishes toward the infrared. Melanosomes, which are melanocyte-specific organelles, densely packed with melanin, are predominantly found within melanocytes. They vary in size according to their genetic origin; black skin typically containing larger melanosomes than lightly pigmented, white skin. Based on melanosome size, the calculated thermal relaxation time for these organelles is around 10 nsec. On the other hand, melanocytes are approximately 7 $\mu$m in diameter, with thermal relaxation times around 1 $\mu$sec. Thermal relaxation time in both instances is defined as the time taken for a structure to cool to 50 % of its peak temperature immediately after laser exposure.

Recent studies have applied the technique of selective photothermolysis to specifically destroy melanosomes using the XeF pulsed excimer in-vitro and the Q-switched ruby lasers in-vivo. Histologically, both these studies demonstrated melanosomal injury that was associated with disruption of melanocytes as well as melanin-containing basal keratinocytes. In addition, there was also evidence of follicular damage after exposure of pigmented guinea pig skin to the Q-switched ruby laser.

DISCLOSURE OF THE INVENTION

In accordance with the present invention, specific laser parameters are established to obtain effective treatment of cutaneous pigmented lesions, particularly epidermal lesions, while minimizing damage to normal pigmented cells. Specifically, effective treatment with minimal damage has been obtained with a laser having a wavelength of about 500 nm, a pulse duration of about 500 nsec, and fluence (energy density) of about 3 $J/cm^2$. The preferred spotsize is 3 mm.

To minimize damage, wavelength should be less than 600 nm. Due to known problems of mutagenesis, the wavelength should not be less than 345 nm.

The fluence may range from 1.0 to 10 $J/cm^2$ through the full range of wavelengths, but is preferably within the range of 2 to 4 $J/cm^2$ for 504 nm light. Pulse durations approaching 1 $\mu$sec may be used but at 1 $\mu$sec recurrence is expected. Shorter pulse durations should minimize damage to normal tissue. Shorter pulses increase the laser intensity for a given fluence, and durations of less than 100 nsec with 2 $J/cm^2$ may stress the optical components of the system, particularly a fiber-optic delivery mechanism.

To avoid pigmentary incontinence of the epidermal pigment resulting from laser irradiation and to get better access to dermal pigment to effectively treat deeper pigmented lesions, a proposed method of treating dermal lesions is to create a window in the epidermis using the above defined laser parameters and then treating the deeper cells with a laser having parameters specific to those cells. It is expected that longer wavelengths will be optimal to achieve such depths of penetration.

DESCRIPTION OF PREFERRED EMBODIMENTS

A wide range of experimental treatments have been performed on the normally pigmented skin of miniature black pigs and those have been followed by extensive clinical studies. A first set of experiments was performed to identify shorter wavelengths in the green portion of the spectrum for the minimization of dermal damage, particularly pigmentary incontinence, as well as regeneration of normal pigment cells. A second set of experiments using the optimum laser wavelength of 504 nm has identified shorter pulse durations as preferred for minimizing damage. Finally, clinical studies of human patients have demonstrated that laser light of the shorter wavelengths and shorter pulse durations is most effective in treating the pigmented lesions where the fluence is about 3 $J/cm^2$. Limited human pigmented lesion studies have demonstrated lack of effectiveness at 694 nm and 750 nm.

Figure 1:
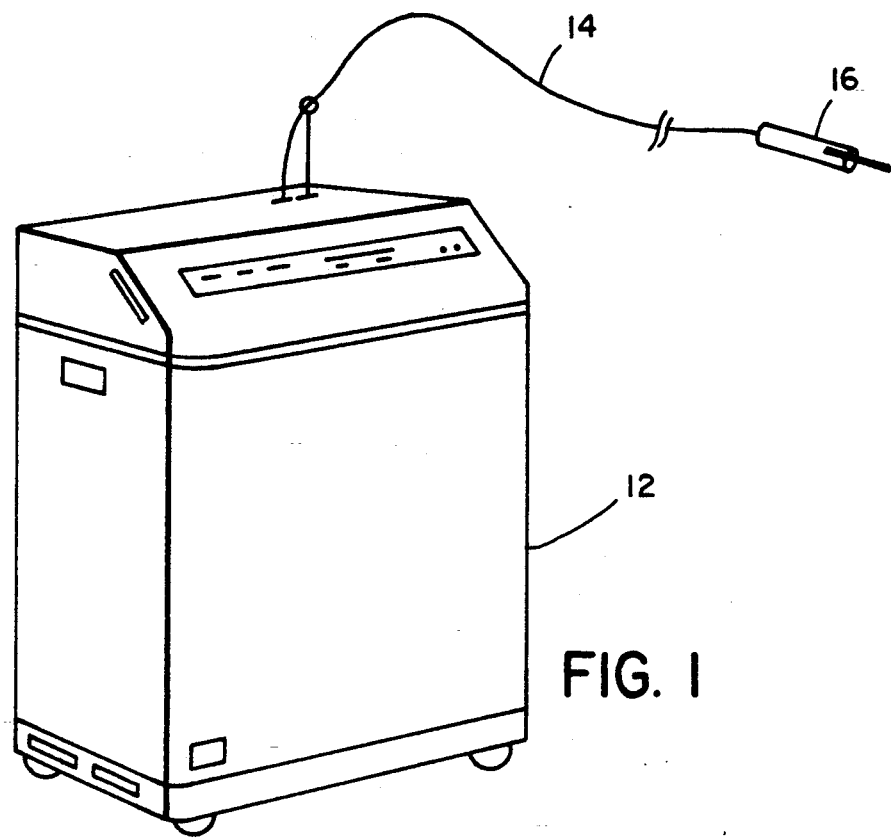
FIG. 1 illustrates a laser having a fiber and handpiece delivery system for practicing the invention.
Figure 2:
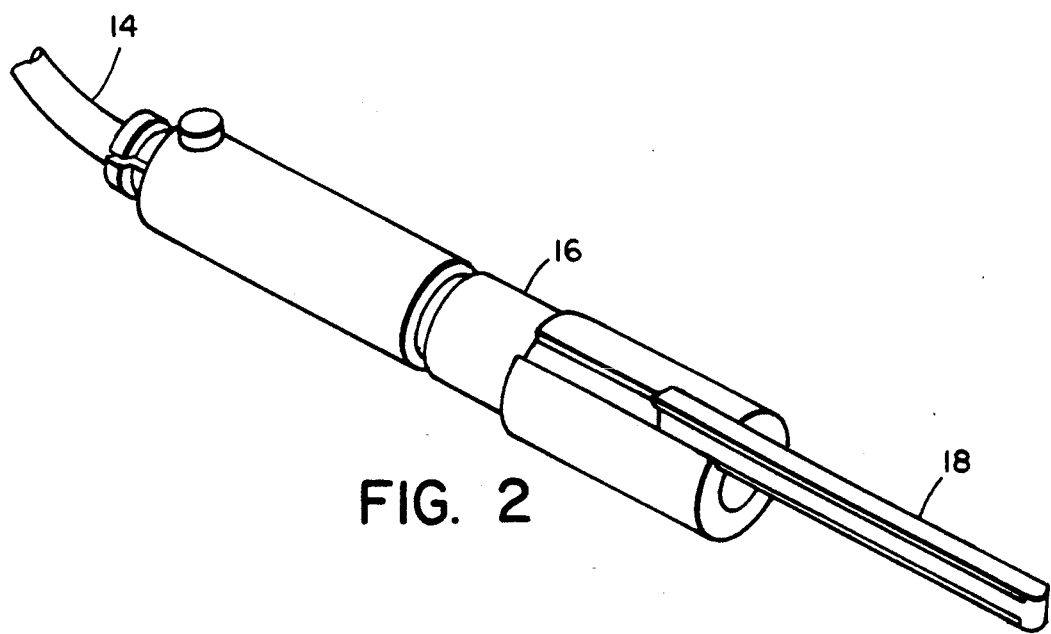
FIG. 2 is an enlarged perspective view of the handpiece.

In the experiments, a Model SLL500-M flashlamp-pumped tunable dye laser system 12 supplied by Candela Laser Corporation has been used. The light is delivered through a 1 mm diameter optical fiber cable 14 to a handpiece 16 to illuminate a spot of 1 to 3 mm with a single pulse. The handpiece, illustrated in FIG. 2, is model number 7040-00-6231 supplied by Candela Laser Corporation. Two lenses in the handpiece image the distal end of the fiber to a larger spot adjacent to the end of a positioning extension 18. By selection of the lenses, the spotsize can be varied. By movement of the handpiece and irradiation of adjacent spots, a test site of about 0.5–1.0 cm × 0.5–1.0 cm is irradiated at a selected dose.

In the first set of experiments on normal black pig skin, the tunable dye laser was tuned to 504, 590, 694, 720 and 750 nm using a variety of dye mixtures. The laser had a pulse duration of 500 nsec. Energy densities ranging from 0.25 to 3.0 J/cm² at 0.25 J/cm² increments, and at 4.0, 5.0, 6.0 and 7.0 J/cm² were delivered to pigmented skin at a spotsize of 3 mm diameter. The skin was irradiated at each energy density for each of the five wavelengths tested. Skin biopsies were taken at each energy density from each of the five wavelengths immediately and at 4, 16, 23 and 33 days after laser exposure. These experiments were published by Sherwood et al., "Effect of wavelength on cutaneous pigment using pulsed irradiation," The Journal of Investigative Dermatology, Vol. 92, No. 5, May 1989.

Exposure of skin to energy densities of at least 5 J/cm² for 590 and 694 nm and 4.0 J/cm² for 720 and 750 nm resulted in sub-epidermal clefts accompanied by epidermal necrosis. No sub-epidermal clefts or epidermal necrosis were observed after exposure of skin to 504 nm irradiation, not even at the highest energy density of 7.0 J/cm². In addition to epidermal injury, dermal damage consisting of collagen bundle separation accompanied by changes in the tinctorial quality of the bundles were observed in biopsies taken from the skin exposed to 7.0 J/cm². at the four wavelengths other than 504 nm. The extent of dermal injury appeared dependent on the wavelength; the most severe occurring at 750 nm. From biopsies, pigmentary incontinence (pigment dropping to the dermal layer) was evident. Its severity increased with increased energy density and wavelength.

Although pigment was destroyed using all wavelengths, repigmentation occurred more rapidly for the 504 nm irradiation. For the 504 nm irradiation, repigmentation was complete by the thirty-third day after exposure. Repigmentation followed sequentially by order of wavelength, with the 750 nm irradiated skin taking up to six weeks for its pigment to return to normal.

In the second set of experiments, miniature black pig skin was again irradiated. Using a 504 nm laser and 3 mm diameter spotsize, the effect of pulse durations of 100, 150, 250 and 500 nsec at fluences from 1.5 to 4.0 J/cm², at 0.5 J/cm² increments, were examined. Biopsies were taken immediately and at 7, 14 and 28 days after irradiation and were processed for light microscopy. The most severe damage was observed in skin exposed to pulse durations of 250 and 500 nsec. Epidermal necrosis, dermal-epidermal separation and pigmentary incontinence were not only more severe, but also occurred at significantly lower fluences than was evident in skin exposed to 100 and 150 nsec pulse durations. Although the normal cells repigment, the unsightly damage remains.

In the final clinical studies with human patients, superficial benign cutaneous pigmented lesions had been treated by using the pulse irradiation. Fifty-two patients have been treated variously for the following: lentigines, solar keratoses/'lentignes', cafe' au lait, seborrheic keratoses, hyperpigmentation associated with morphoea, nevus spilus.

Generally, the lesions have been exposed to 504 nm laser irradiation. Pulse durations of 250 nsec, 500 nsec and 1 μsec have been used with fluence ranging from 1.5 to 3.5 J/cm² for each pulse duration. A 3 mm diameter spotsize was used with the 500 nsec and 1 μsec pulse durations. Because of limits in energy available from the particular laser used, a 2 mm diameter spotsize was used with 250 nsec pulse durations. A 1 mm diameter spotsize was used in limited tests of 6 to 8 J/cm², but excessive dermal damage was noted. This is consistent with findings presented in Tan et al., "Spotsize effects on guinea pig skin following pulsed irradiation," The Journal of Investigative Dermatolozy, Vol. 90, No. 6, Jun. 1988. At all pulse durations, incomplete lightening was found at 2 J/cm² and 2.5 /cm² . The 3.0 J/cm² was found to be the most effective dose. The 3.5 J/cm² was only used in a limited number of tests where insufficient response was obtained at 3.0 J/cm² and was effective. With the 1 μsec pulse duration, the lesions cleared but recurred. At 500 nsec, nonrecurring clearance was obtained. At 250 nsec, clearance was also obtained, and we are awaiting final results. Clinical observations indicate minimal dermal damage without noticeable pigmentary incontinence.

With limited tests at 504 nm and 4 J/cm², some permanent loss of normal pigment and undesirable surface changes were noted. However, with appropriate selection of other parameters, higher fluences may be feasible.

Limited tests of a 694 nm Q-switched ruby laser having a pulse duration of 20 nsec and fluence of 5 J/cm² proved ineffective in removing the lesions. Similarly, a Q-switched alexandrite laser of 760 nm, 100 nsec and 3 J/cm² was ineffective in treating the lesion with a 2 mm spotsize.

Limited tests at 577 nm, 360 μsec resulted in clearance of the lesion but with recurrence. However, lesions are expected to be effectively treated with that wavelength at shorter pulse durations. To minimize adverse effects, particularly due to pigmentary incontinence, wavelengths of about 600 nm or less are judged best from the first set of experiments.

Although 504 nm is the shortest wavelength tested, it is the most effective, and it is expected that shorter wavelengths within the melanin absorption spectrum will provide desirable results. Due to concerns for mutagenesis, wavelengths of less than 345 nm should not be used. It is postulated that the shorter wavelengths are most effective with least damage because they are absorbed by blood in the dermis and thus create thermal effects which minimize pigmentary incontinence.

It is expected that the acceptable fluence range is a function of wavelengths. At 504 nm, some effect on melanin is noted at 2 J/cm², and damage is seen above 4 J/cm² . The depth of penetration in caucasian skin, which is inversely related to absorption, for 350 nm, 500 nm, 600 nm and 700 nm is about 60 μ, 230 μ, 550 μ and 750 μ, respectively. Thus, expected ranges of effect without damage, based on the 2 to 4 J/cm² range at 504 nm, is about 0.5 to 1.0 J/cm² for 345 nm, and 5 to 10 J/cm² for 600 nm. In general, it is expected that fluences of 1 to 10 J/cm² will be used for wavelengths of 345 nm to 600 nm.

Although indications are that pulse durations of even less than 500 nsec are desirable, at pulse durations of less than 100 nsec, delivery systems such as articulated arms or liquid-filled light guides may be required, and general stress on system optics may be excessive. However, with shorter pulse durations, it is expected that lesser fluences may be used.

On the other hand, treatment of pigmentary lesions in the dermis are of interest, and longer wavelengths are expected to be more effective due to greater depths of penetration. A problem encountered with longer wavelengths is that of pigmentary incontinence where pigment from the epidermis is driven to the lower dermis. One means of treating the deeper lesions with longer wavelengths without pigmentary incontinence is to remove the pigment in the epidermis using the shorter wavelengths and subsequently treat the lower regions with longer wavelengths. Thus, the shorter wavelengths remove the pigment from the epidermis to create a window through which the light can pass into the dermis. Without pigment in the epidermis, illumination using the longer wavelengths cannot cause the pigmentary incontinence.

While this invention has been particularly shown and described with references to preferred embodiments thereof, it will be understood by those skilled in the art that various changes in form and details may be made therein without departing from the spirit and scope of the invention as defined by the appended claims.

We claim:

1. A method of treating melanin-based pigmented lesions in human skin comprising irradiating an epidermis with laser radiation of wavelength between 345 and 600 nm, fluence of 1 to 10 J/cm$^2$ and pulse duration of less than 1 μsec.

2. A method as claimed in claim 1 wherein the pulse duration is substantially 100 nsec.

3. A method as claimed in claim 1 wherein the pulse duration is substantially 500 nsec or less.

4. A method as claimed in claim 1 wherein the laser irradiates a spot of substantially 1 to 3 mm diameter.

5. A method as claimed in claim 1 wherein the fluence is less than 4 J/cm$^2$.

6. A method as claimed in claim 5 wherein the fluence is at least 2 J/cm$^2$.

7. A method as claimed in claim 6 wherein the pulse duration is substantially 500 nsec or less.

8. A method as claimed in claim 7 wherein the pulse duration is substantially 100 nsec.

9. A method of melanin-based treating epidermal pigmented lesions in human skin comprising irradiating an epidermis with laser radiation of wavelength about 500 nm, fluence of 2 to 3 J/cm$^2$ and pulse duration of 500 to 600 nsec or less.

10. A method as claimed in claim 9 wherein the laser irradiates a spot of 1 to 3 mm diameter.

11. A method as claimed in claim 9 wherein the pulse duration is substantially 100 nsec.

* * * * *

UNITED STATES PATENT AND TRADEMARK OFFICE
CERTIFICATE OF CORRECTION

PATENT NO. : 5,312,395
DATED : May 17, 1994
INVENTOR(S) : Tan et al.

It is certified that error appears in the above-indentified patent and that said Letters Patent is hereby corrected as shown below:

In column 5, line 20, insert --epidermal-- before "pigmented".

In column 5, line 22, insert --layer of said skin-- before "with".

In column 6, line 15, replace "melanin-based treating" with --treating melanin=based--.

In column 6, line 17, insert --layer of said skin-- before "with" and delete "about".

In column 6, line 18, insert --to 600-- after "500" and replace "3" with --4--.

In column 6, line 19, delete "to 600".

Signed and Sealed this

Fourteenth Day of February, 1995

Attest:

BRUCE LEHMAN

*Attesting Officer*   *Commissioner of Patents and Trademarks*